(12) United States Patent
Lambert et al.

(10) Patent No.: US 9,726,630 B2
(45) Date of Patent: Aug. 8, 2017

(54) SENSOR FOR FLUID-SOLUBLE GAS

(71) Applicant: KONINKLIJKE PHILIPS N.V., Eindhoven (NL)

(72) Inventors: Niek Lambert, Waalre (NL); Laurentina Johanna Huijbreghts, Eindhoven (NL); Joost Kahlman, Tilburg (NL); Hans Willem Van Kesteren, Eindhoven (NL); Anton Vink, Valkenswaard (NL)

(73) Assignee: Koninklijke Philips N.V., Eindhoven (NL)

( * ) Notice: Subject to any disclaimer, the term of this patent is extended or adjusted under 35 U.S.C. 154(b) by 440 days.

(21) Appl. No.: 14/354,174

(22) PCT Filed: Oct. 26, 2012

(86) PCT No.: PCT/IB2012/055911
§ 371 (c)(1),
(2) Date: Apr. 25, 2014

(87) PCT Pub. No.: WO2013/061293
PCT Pub. Date: May 2, 2013

(65) Prior Publication Data
US 2014/0238855 A1    Aug. 28, 2014

Related U.S. Application Data

(60) Provisional application No. 61/552,638, filed on Oct. 28, 2011.

(51) Int. Cl.
*G01N 27/26* (2006.01)
*G01N 7/00* (2006.01)
(Continued)

(52) U.S. Cl.
CPC .......... *G01N 27/304* (2013.01); *A61B 5/1477* (2013.01); *A61B 5/14542* (2013.01); *G01N 27/307* (2013.01); *G01N 27/4045* (2013.01)

(58) Field of Classification Search
CPC .......... G01N 27/26; G01N 7/00; G01N 21/00; G01N 27/00; G01N 33/00; G01N 15/06; G01N 33/48
(Continued)

(56) References Cited

U.S. PATENT DOCUMENTS 3,730,868 A    5/1973   Niedrach
4,227,984 A *  10/1980  Dempsey et al. ............ 204/408
(Continued)

FOREIGN PATENT DOCUMENTS

CN    102056540 A    5/2011
EP    1024357        8/2000
(Continued)

OTHER PUBLICATIONS

P. Mirtaheri et al., "A new Biomedical Sensor for Measuring PCO2", institute of Physics Publishing; Physiological Measurement 25 (2004) pp. 421-436.
(Continued)

*Primary Examiner* — Brian J Sines (57) ABSTRACT

For measuring concentrations of fluid-soluble gases with improved drift stability and low production costs, thus dispensing with tedious calibration and/or drift correction routines and re-membraning procedures, a sensor and a system are provided, comprising at least two electrodes, which are covered by sensor fluid at at least one detection site; and an ion-balancing means (50), for example a mixed-bed ion-exchange resin, in contact with the sensor fluid for removing polluting ions.

18 Claims, 7 Drawing Sheets

(51) Int. Cl.

| | | |
|---|---|---|
| *G01N 21/00* | (2006.01) | |
| *G01N 27/00* | (2006.01) | |
| *G01N 33/00* | (2006.01) | |
| *G01N 15/06* | (2006.01) | |
| *G01N 33/48* | (2006.01) | |
| *G01N 27/30* | (2006.01) | |
| *A61B 5/145* | (2006.01) | |
| *G01N 27/404* | (2006.01) | |
| *A61B 5/1477* | (2006.01) | |

(58) Field of Classification Search
USPC .... 422/68.1, 82.01, 82.02, 82.03, 82.04, 83, 422/98; 204/431, 432, 433, 435
See application file for complete search history.

(56) References Cited

U.S. PATENT DOCUMENTS

| | | | |
|---|---|---|---|
| 4,228,400 A | 10/1980 | Bruckenstein et al. | |
| 4,473,456 A | 9/1984 | Hawkins | |
| 5,164,053 A * | 11/1992 | Razaq et al. | 205/784 |
| 5,346,604 A | 9/1994 | Van Sin et al. | |
| 5,788,828 A * | 8/1998 | Nakatsu et al. | 204/632 |
| 6,678,554 B1 * | 1/2004 | Sun et al. | 604/20 |
| 2011/0079523 A1 | 4/2011 | Offenbacher et al. | |
| 2014/0238855 A1 | 8/2014 | Lambert et al. | |

FOREIGN PATENT DOCUMENTS

| | | |
|---|---|---|
| GB | 2100864 | 1/1983 |
| GB | 2208006 | 2/1989 |
| JP | S57116244 A | 7/1982 |
| JP | S593345 A | 1/1984 |
| JP | S6074043 A | 4/1985 |
| JP | S60162950 A | 8/1985 |

OTHER PUBLICATIONS

J.H. Storre et al., "Transcutaneous Monitoring as a Replacement for Arterial PCO2 Monitoring During Nocturnal Non-Invasive Ventilation", Respiratory medicine (2001) 105, pp. 143-150.

C. Tronstad et al., "Early Detection of Cardiac Ischemia Using a ConductometricPCO2 Sensor: Real-Time Drift Correction and Parameterization", Physiological Measurement 31, (2010), pp. 1241-1255.

A.R. Varlan et al., Micromachined Conductometric P(CO2) Sensor, Sensors and Actuators B 44 (1997), pp. 309-315.

* cited by examiner

SENSOR FOR FLUID-SOLUBLE GAS

CROSS-REFERENCE TO PRIOR APPLICATIONS

This application is the U.S. National Phase application under 35 U.S.C. §371 of International Application Serial No. PCT/IB2012/055911, filed on Oct. 26, 2012, which claims the benefit of U.S. application Ser. No. 61/552,638, filed on Oct. 28, 2011. These applications are hereby incorporated by reference herein.

FIELD OF THE INVENTION

The present invention relates to a sensor for determining concentrations of fluid-soluble gases and a system comprising such a sensor.

BACKGROUND OF THE INVENTION

In recent years, monitoring and treatment of patients at home becomes more and more important in view of costs as well as convenience. For these patient monitoring systems, sensors are required that are easy to use and do not degrade the compliance of the patients. For instance, in order to treat patients with chronic respiratory failure at home, future non-invasive ventilation systems may incorporate a module for non-invasive measurement of blood gas concentrations to check the effectiveness of ventilation. For non-invasive $CO_2$ blood gas monitoring, transcutaneous sensors (measurement through the skin) seem to be the best solution.

In general, transcutaneous sensors consist of a membrane, which is permeable for small neutral molecules in the gas or vapour phase (like $CO_2$, $O_2$, $N_2$, and $H_2O$), but not for ions nor large molecules, and of a sensor fluid, into which the gas molecules diffuse. In the example of $CO_2$ sensors, the fact is used that, when $CO_2$ dissolves in water, part of it will form carbonic acid ($H_2CO_3$), which in another equilibrium reaction with $H_2O$ forms $H_3O^+$ and $HCO_3^-$. By measuring the amount of these ions, the $CO_2$ pressure on the other side of the membrane, which is in equilibrium with the sensor fluid, can be derived.

However, current transcutaneous systems are optimized for prolonged use in the hospital and need placement of the sensor on the skin by trained staff. A further disadvantage of these sensors is that they need replacing of the membrane and of the sensor fluid approximately every two weeks (so-called re-membraning). This is required on the one hand, since the membrane gets dirty on the outside, e.g. by fatty substances from the skin, which block the membrane pores through which the gas molecules to be detected should flow. On the other hand, conventional transcutaneous sensors suffer from sensor fluid loss, such as fluid evaporation through the membrane. Furthermore, ions leach out from the sensor housing, glue or other sensor parts into the sensor fluid, thus polluting the sensor fluid. These unwanted "polluting" ions in the sensor fluid shift the equilibria of the above-mentioned chemical reactions and distort the measurement results. Hence, conventional fluid-based sensors for fluid-soluble gas molecules are subject to drift during the measurements and need calibration before use. Therefore, these prior art sensors are rather inconvenient to operate and require expertise in application and maintenance, thus inappropriate for use at home or by the patient himself.

U.S. Pat. No. 4,228,400 describes a conductometric gas analysis cell comprised of a porous Teflon membrane supporting interdigitated electrodes, which separates a thin layer of deionized water from a gas phase to be analyzed.

SUMMARY OF THE INVENTION

It is an object of the present invention to provide a sensor and a system for measuring the concentration of fluid-soluble gases with improved drift stability and low production costs, thus dispensing with tedious calibration and/or drift correction routines and re-membraning procedures.

The object is solved by the features of the independent claims.

The invention is based on the idea to add an ion-balancing means to a sensor fluid for removing polluting ions from the sensor fluid. Preferably, the ion-balancing means does not influence concentration measurements of the fluid-soluble gas to be measured, i.e. measurements with and without ion-balancing means are about the same. This may be realized by a sensor design such that timescales for measurement and for removal of polluting ions are different. For instance, selectivity, affinity, amount and/or spatial arrangement of the ion-balancing means may be chosen accordingly, so that polluting ions are removed without influencing the measurement based on ions originating from the dissolved gas to be sensed. Here, polluting ions may denote ions different from those ions originating from the fluid-soluble gas. However, this is not necessarily the case, so that polluting ions may also denote ions that remain in the sensor fluid after having been measured and should be removed in the long term. Due to the removal of polluting ions, no calibration is needed before use nor a drift correction of the measurements is required.

According to one aspect of the present invention, a sensor for measuring concentrations of fluid-soluble gas comprises at least two measurement electrodes, which are at least partially covered by a sensor fluid. Preferably, the electrodes are covered by the sensor fluid at at least one detection site, i.e. such that they are electrically connected to each other by means of the sensor fluid. Here, the detection site refers to the site of actual measurement in the sensor, e.g. the site at the electrodes, which are predominantly relevant for the measurement. For instance, in a conductometric sensor design, the detection site may refer to the fluid volume or also to the site of the electrodes, between which the measurement current flows. In addition, the sensor includes an ion-balancing means, which is in contact with the sensor fluid and adapted to remove polluting ions from the sensor fluid. This may be based only on diffusion effect, i.e. the sensor fluid is not actively pumped. By these means, the ion-balancing means can remove polluting ions, e.g. leaching out from the sensor housing, glue or other parts of the sensor, which would distort the measurement.

In one embodiment, the removal of polluting ions by the ion-balancing means may be performed on a different timescale than measuring ions originating from the fluid-soluble gas, e.g. differing by a factor of at least about 10, 100 or even 1000. In particular, the sensor may be designed such that changes in the gas concentration to be detected are on a shorter time scale than the time scale for the occurrence of contamination. By these means, offset and/or drift in the sensor measurement may be reduced, while maintaining the sensitivity for fluid-soluble gas to be detected.

For realizing these different timescales, an amount and/or kind of the ion-balancing means and/or the sensor geometry may be chosen such that on the relevant timescales, the polluting ions are sufficiently removed by the ion-balancing means, while the amount of ions originating from the dissolved gas is in the same equilibrium with the gas pressure to be measured as it would be without ion-balancing means. Preferably, the ion-balancing means may be arranged spaced apart by a predetermined distance from the electrodes or at least from the detection site of the electrodes. For instance, the distance between the ion-balancing means and the detection site may be chosen to be larger than a thickness of sensor fluid at the detection site, i.e. on the electrodes. This thickness of sensor fluid may be determined by the sensor geometry, e.g. by a height of a fluid channel crossing the electrodes at the detection site or a distance between the detection site of the electrodes and a membrane, through which the gas enters. Additionally or alternatively, a distance between the ion-balancing means and the detection site may be larger than a distance between the electrodes themselves at the detection site. Thus, a sensor is provided comprising an area, in which ion-balancing means is stored and which is sufficiently far apart from an area, where a signal is measured. This ensures that the sensor performance is not affected by the ion-balancing means.

In a further embodiment, the amount of the ion-balancing means is adjusted to one or more parameters of the sensor, such as a geometry of the sensor, a size of the sensor, a measurement principle of the sensor, the type of sensor fluid comprised in the sensor and the type of gas to be measured. Alternatively or additionally, the type of the ion-balancing means may be adjusted to one or more of these parameters, thus adapting affinity and/or selectivity of the ion-balancing means to the respective application. For instance, the sensor type may relate to a chemo-optical, conductometric, potentiometric and/or pH-based sensor. Accordingly, the sensor may comprise as sensor fluid at least one of water, de-ionized water, electrolyte, buffer solution or the like. Fluid-soluble gases, which can be measured by the sensor, preferably include blood gases, such as $CO_2$, $O_2$, $N_2$, but also other fluid-soluble gases such as gases dissolving in ions including $Cl^-$, $F^-$, $Na^+$, or $NH_3^+$. According to this embodiment, the parameters of ion-balancing means may be chosen such that the timescales for changes in the gas concentration to be measured are shorter than the timescales for the occurrence of contamination.

In a preferred embodiment, the ion-balancing means may have a low affinity for ions of the dissolved gas to be measured. For instance, for measuring a $CO_2$ gas pressure, the ion-balancing means may have low affinity for at least one of the ions, into which $CO_2$ dissolves, e.g. $H_3O^+$, $H^+$, $HCO_3^-$ and $OH^-$. This further ensures that the addition of the ion-balancing means does not influence the measurement sensitivity of the sensor.

The ion-balancing means may include at least one of a substance capable of trapping, absorbing or exchanging polluting ions. Thus, the ion-balancing means may include an ion-exchange polymer or ion-exchange resin, which absorb ions from a solution and replace them by other ions. Preferably, a mixed-bed ion-exchange resin is used, consisting of two materials: one easily absorbing many kinds of negative ions and replacing them by $OH^-$, the other easily absorbing many kinds of positive ions and replacing them by $H^+$. In this case, the $OH^-$ and $H^+$ ions created in this manner react with each other, forming $H_2O$. By these means, pollution of the sensor fluid can be avoided or at least reduced, so that sensor drift is also reduced.

In one embodiment, the at least two electrodes are arranged concentrically and/or have a ring-shaped structure. Alternatively or additionally, the electrodes may be arranged in an interdigitated or comb-like structure. The electrodes may also be laminated in some sensor parts, e.g. in a sensor housing or in walls of a fluid channel. However, a simple linear geometry, in which the electrodes are arranged in parallel to each other, is also possible.

Furthermore, the ion-balancing means may be arranged in a centre of the sensor. Alternatively or additionally, the ion-balancing means may be arranged at one or more side portions and/or at the circumference of the sensor. Then, the ion-balancing means may be closer to the source of pollution. Moreover, an arrangement of the ion-balancing means in a boundary area of the sensor may provide more space for adding ion-balancing means and facilitate rinsing of the sensor for initial cleaning and bubble-free filling, thus simplifying the production. Possibly, resin or polymer beads are used as ion-balancing means. The ion-balancing means may be immobilized using glue or a mesh. Alternatively or additionally, the ion-balancing means may be immobilized by arrangement within a semi-separated compartment on a sensor substrate. By these means, it can be ensured that the ion-balancing means is kept away from the detection site of the electrodes and thus cannot disturb the measurement.

In a further preferred embodiment, the sensor includes at least one membrane, which is at least partially in contact with the sensor fluid. The sensor may further comprise a substrate or housing, in which the electrodes and/or the ion-balancing means may be arranged. Also, the housing may be filled at least partially with sensor fluid. Moreover, the housing may be covered at least partially by a membrane, which may be permeable for gas molecules to be measured. For instance, the membrane covers at least partially one side of the housing. The membrane may be fixed to the housing by means of an o-ring, welding and/or glue. Thus, the membrane may be in contact with a sample volume, so that the gas to be measured may diffuse from the sample volume into the sensor fluid and dissolve there into ions. Preferably, the membrane is impermeable for ions and/or the sensor fluid. By these means, pollution and/or loss of sensor fluid can be kept low, so that sensor drift is reduced. In a further preferred embodiment, the membrane is only in contact with the sensor fluid close to the detection site, i.e. the sensor fluid above the detection site of the electrodes may be covered by the membrane. For instance, the electrodes may be arranged at a bottom surface of the housing. Then, the upper side of the sensor housing may have one or more openings, which are covered by the membrane and arranged above the detection sites of the electrodes. Alternatively or additionally, the electrodes may be laminated within walls of the sensor housing, e.g. within side walls of fluid channels or the like. By providing a solid housing except for the openings covered by the membrane above the detection site, the mechanical stability of the sensor is enhanced and the membrane is better supported. Besides, fluid evaporation can be reduced due to the small membrane-fluid interface.

In another embodiment, the sensor may comprise one or more fluid channels, which intersect with the electrodes at least at the detection site. Preferably, the fluid channels connect the detection site of the electrodes with the site, at which the ion-balancing means is arranged. Thus, the ion-balancing means may remove polluting ions from the detection volume, although the ion-balancing means may be spaced apart from the detection site. The fluid channel may be at least partially defined by a membrane, e.g. the membrane may cover the fluid channel at least on top of the detection site of the electrodes. Moreover, the fluid channel crossing the electrodes at the detection site may determine the relevant fluid volume at the detection site. Preferably, a height of the fluid channel at the detection site is low, e.g.

smaller than one millimeter. This may drastically influence the sensitivity and measurement speed of the sensor, since the dissolved gas ions need to diffuse to the electrodes.

In a preferred embodiment, a fluid reservoir for storing sensor fluid may be provided, which is connected to the detection site. From the fluid reservoir, the space near the electrodes may be filled up with sensor fluid. The fluid reservoir may be a chamber or compartment filled with sensor fluid, which is semi-separated from the detection site, i.e. only allowing for a restricted fluid exchange or diffusion, while the fluid volume in the fluid reservoir does not contribute to the detection volume. By these means, a certain volume of sensor fluid at the detection site may be maintained. In particular, a small thickness of sensor fluid or a small detection volume may be provided at the detection site, while sufficient covering of the electrodes with sensor fluid is guaranteed by the large volume of sensor fluid in the fluid reservoir. Hence, loss of sensor fluid, e.g. by evaporation through a membrane, and resulting rise of ion concentration can be compensated. The fluid reservoir may be spaced apart from the detection site on the electrodes. Then, the fluid reservoir and the detection site may be connected by at least one capillary and/or hydrophilic and/or hygroscopic structure. For instance, one or more fluid channels may connect the fluid reservoir and the at least one detection site, wherein the fluid channel has a capillary structure and/or a hydrophilic and/or a hygroscopic coating or surface. Additionally or alternatively, the area near the electrodes may be made hydrophilic, e.g. using a plasma treatment. Thus, sensor fluid is automatically guided to the space near the electrodes, e.g. to the detection site. The fluid reservoir may be defined by walls of the sensor housing except for one or more openings connected to the detection site. Thus, the fluid reservoir may be isolated from the outside of the sensor, so that fluid evaporation may be further reduced.

When using an embodiment with fluid reservoir, the ion-balancing means is preferably arranged within the fluid reservoir. Thus, the sensor performance is even more improved, while providing a simple and compact sensor design advantageous for portable sensors or for sensors to be used at home.

In addition, the sensor may include a release means that allows the fluid reservoir to release the sensor fluid to the detection site. For instance, this may be realized as a moveable and/or flexible wall of the fluid reservoir and/or a pre-arranged site where a gas-bubble is trapped that can easily grow as the sensor fluid from the fluid reservoir slowly replenishes any evaporation loss at the detection site. A gas-bubble may for example be intentionally left in the sensor. Alternatively or additionally, the release means may be hydrophobic. Possibly, a semi-separated compartment may be used as a release means filled with gas and/or connected to the fluid reservoir, e.g. by hydrophobic channels. However, it may be favorable to avoid bubbles at the detection site, or a depressed membrane, or even to avoid bubbles at all in the sensor, e.g. by using a flexible fluid reservoir filled with degassed sensor fluid and packaged gas-tight. In this case, the release means may be formed as a site in the fluid reservoir that is separate from the detection site and/or more favorable for bubble-forming.

The sensor according to any of the described embodiments may include a conductometric, a potentiometric, a chemo-optical or a pH-based sensor. Of course, the sensor fluid and/or the electrodes and/or the ion-balancing means may be adapted to the corresponding sensor type. Moreover, the sensor according to any of the described embodiments of the present invention may be integrated in and/or combined with other fluid-based sensors, e.g. transcutaneous $O_2$ sensors or the like.

Preferably, the sensor is configured as a sensor for measuring blood-gas concentrations, such as $CO_2$ pressure. For this, the sensor relates preferably to a non-invasive or transcutaneous sensor for biomedical applications, e.g. for measuring a gas concentration through the skin or in the exhaled breath or for measuring a gas concentration in the body using a catheter. Furthermore, the sensor may be operable with a patient monitoring and/or ventilation system, e.g. for patient treatment at home. The sensor may be portable, e.g. provided with at least one of fixing means for fixing the sensor to a body part of the patient, a power source, a transmission unit for transmitting the sensed data and/or receiving configuration data, a chip for storing and/or processing the sensed data and the like. Further, the sensor may be disposable due to low production costs. This is in particular useful, if the ion-balancing means has limited capacity, so that on the longer term, its effectiveness will also be influenced by the dissolved gas acquired during operation. Likewise, a permeability of a sensor membrane may degrade over time due to dirt on the outer surface. Therefore, instead of re-membraning or exchanging the sensor fluid, the sensor may simply be replaced. For storage, the sensor may be packed in a fluid-tight and/or gas-tight sealing, possibly even filled with water or sensor fluid on the outside of the sensor. This avoids fluid evaporation during storage. Gas-tight may be needed to keep atmospheric $CO_2$ and/or $O_2$ out and/or prevent $H_2O$ evaporation.

According to another aspect of the present invention, a system for patient monitoring and/or ventilation of a patient is provided, comprising a sensor according to any of the above-described embodiments of the present invention. By these means, such a system is made easy to use and can be operated by the patient himself. Moreover, the measurements may be performed non-invasive, thus increasing the patient's compliance.

Even though the described embodiments will be explained in particular with reference to a transcutaneous non-invasive $CO_2$ sensor for blood gas monitoring and a patient monitoring and/or ventilation system using the same, the inventive sensor may be readily applied to different fields and other systems as well, such as other blood gas sensors and home healthcare products or in general to sensors for fluid-soluble gases.

DETAILED DESCRIPTION OF THE EMBODIMENTS

According to the present invention, a sensor is provided comprising an area, in which ion-balancing means is stored for removing polluting ions from a detection volume. Thus, the removal of polluting ions can be performed without active pumping of the sensor fluid and is based primarily on ion diffusion in the sensor fluid. There are various types of sensors that can be used, e.g. potentiometric, conductometric and pH-based sensors. From these measurements, the $CO_2$ pressure on the other side of the membrane, which is in equilibrium with the sensor fluid, can be derived.

Sensors based on a potentiometric measurement principle determine the amount of $H_3O^+$ by measuring the potential difference between a reference electrode and an electrode with a $H^+$-selective membrane in the sensor fluid. In potentiometric sensors, dedicated electrode structures are incorporated and the compositions of the electrolyte fluid used as sensor fluid are chosen in such a way that the potentiometric sensor has a good selectivity for the ion to be detected. Yet, in particular reference electrodes in these sensors are prone to drift and all known potentiometric sensors need calibration.

Conductometric sensors on the other side, measure the conductivity of the sensor fluid, which is determined by the total amount of ions in the fluid. In conductometric sensors, the influence of both the effect of leaching of ions from the housing into the sensor fluid and the effect of water evaporation through the membrane are even worse than in potentiometric sensors, as the polluting ions not only shift the equilibria, but also contribute to the conductivity of the sensor fluid, and as a drop in fluid level not only leads to increased ion concentrations, but also influences the paths along which the electrical current can flow. When a conductometric sensor is operated in a contamination-free environment, the dissolved $CO_2$ concentration can be quantitatively linked to the conductivity and calibration is not required. However, conductometric sensors are non-selective and in practice, an offset or drift in conductivity level is easily introduced. According to the present invention, addition of ion-exchange resin enables to reduce the contamination without significantly influencing the dissolved $CO_2$ concentration and enables to restore the quantitative link between conduction level and $CO_2$ concentration.

In the following, the sensor according to the present invention will be exemplified using the example of a transcutaneous conductometric sensor for $CO_2$. However, the present invention is not limited thereto, but the sensor may also be a potentiometric or pH-based sensor or adapted to measure other kinds of fluid-soluble gas.

Figure 1A:
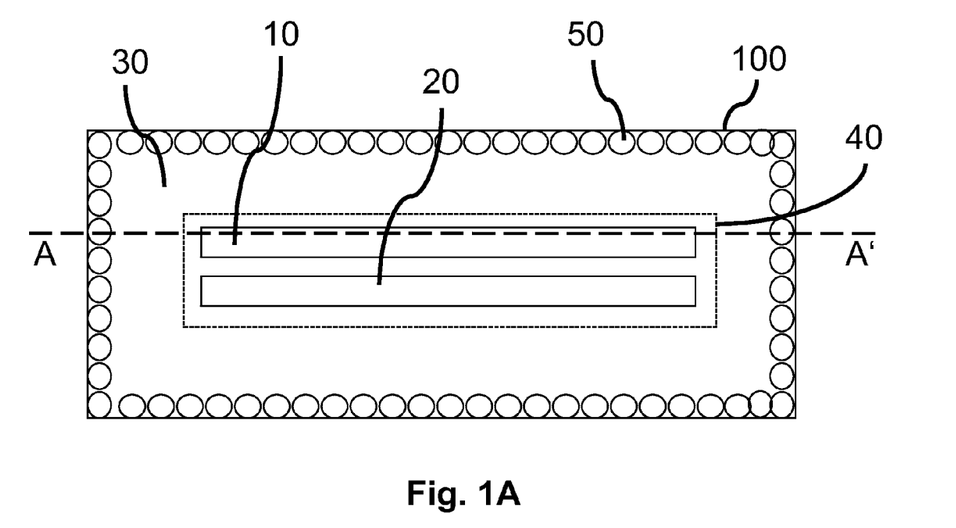
FIG. 1A shows a plan view of an embodiment of a sensor according to the present invention and FIG. 1B shows a cross section of the sensor shown in FIG. 1A along line A-A'.
Figure 1B:
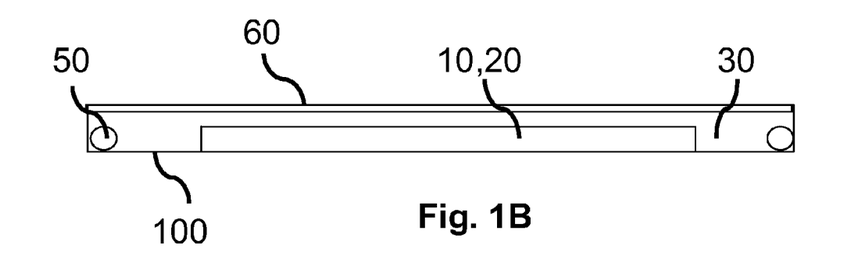

As shown in FIGS. 1A and 1B, the sensor comprises a housing or substrate 100, which is covered by a selective permeable membrane 60 and filled with a sensor fluid 30. In the housing or on the substrate 100, electrodes 10 and 20 are arranged in parallel. The sensor fluid 30 may be a water-based liquid which, apart from water, may contain ions (in particular the ions from sodium bicarbonate). Alternatively, the sensor fluid may include a hygroscopic liquid like propylene glycol or poly(ethylene glycol) or also a polar or non-polar solvent, depending on the gas to detect. Moreover, an ion-balancing means 50 is arranged in a boundary region of the sensor. For instance, an ion-exchange resin in form of beads may be used as an ion-balancing means 50, e.g. a mixed-bed ion-exchange resin that replaces cations by $H^+$ and anions by $OH^-$.

The membrane 60 may be sealed or glued to the housing 100 and is permeable for the gas molecules to be measured. Thus, the gas molecules pass through the membrane 60 and dissolve in the sensor fluid 30 into the corresponding ions. For instance, a PTFE membrane or the like may be used. As explained before, the $CO_2$ molecules will dissolve in water producing $H_3O^+$, $HCO_3^-$ and $OH^-$ ions. The ions will diffuse to the electrodes 10 and 20 and thus increase the conductivity of the sensor fluid 30. Actually, the lightly bound $H^+$ ion in the ion-balancing means 50 really is an $H^+$ ion. But $H^+$ ions in water immediately combine into $H_3O^+$ ions, so that the terms $H^+$ and $H_3O^+$ are more-orless interchangeably in this case.

The ion-balancing means 50 is arranged spaced apart from the detection site 40 (indicated by a dashed box) at the electrodes 10 and 20, where the signal is measured. The ion-balancing means 50 can be immobilized in the housing 100 using glue, a mesh or a membrane or by arranging it in a semi-separated compartment within the housing 100. Hence, the ion-balancing means 50 is spaced apart from the electrodes 10 and 20, but is in contact with the sensor fluid 30. By these means, the ion-balancing means 50 should not influence the measurement itself nor the amount $H_3O^+$ and $HCO_3^-$ ions on timescales that are relevant for the measurement. However, the ion-balancing means 50 should absorbe ions leaching out from the housing 100, glue or other parts of the sensor. These polluting ions should reach and react with the ion-balancing means 50 on longer timescales than those relevant for the measurement. Possibly, the ion-balancing means 50 is chosen such that its affinity for anions coming from the housing or glue is larger than its affinity for $HCO_3^-$.

As an example for an ion-balancing means, a strong mixed-bed ion-exchange resin can be used such as the ion-exchange resin Dowex™ Marathon mr-3. Alternatively, one may also choose a strong cation-exchange resin in combination with a weak anion-exchange resin, because a weak anion-exchange resin can have less effect on the $HCO_3^-$ originating from the $CO_2$ molecules. In general, the anion-exchange resin, which can either be applied in combination with the cation-exchange resin as a mixed-bed resin or separated from the cation-exchange resin, should preferentially have affinities that are higher for polluting ions than for $HCO_3^-$ and $OH^-$. Similarly, the cation-exchange resin should preferentially have a low affinity for $H^+$ and high affinity for polluting ions.

In addition, the sensor may be configured as a portable sensor, e.g. to be attached to a patient's body part for measurement or monitoring. Thus, the sensor may comprise a power supply, such as a battery, or connections for power supply. Likewise, a chip for processing or storing measured data may be provided. In addition or alternatively, a transmission unit may be provided for transmitting measured data to a server unit of a patient monitoring system or the like. The transmission unit may also be adapted to receive setup data etc. By these means, a sensor can be provided, which is portable without any electrical connections or data connections. Moreover, the sensor according to the present invention can be integrated in a system, e.g. a ventilation system or a patient monitoring system.

Figure 2A:
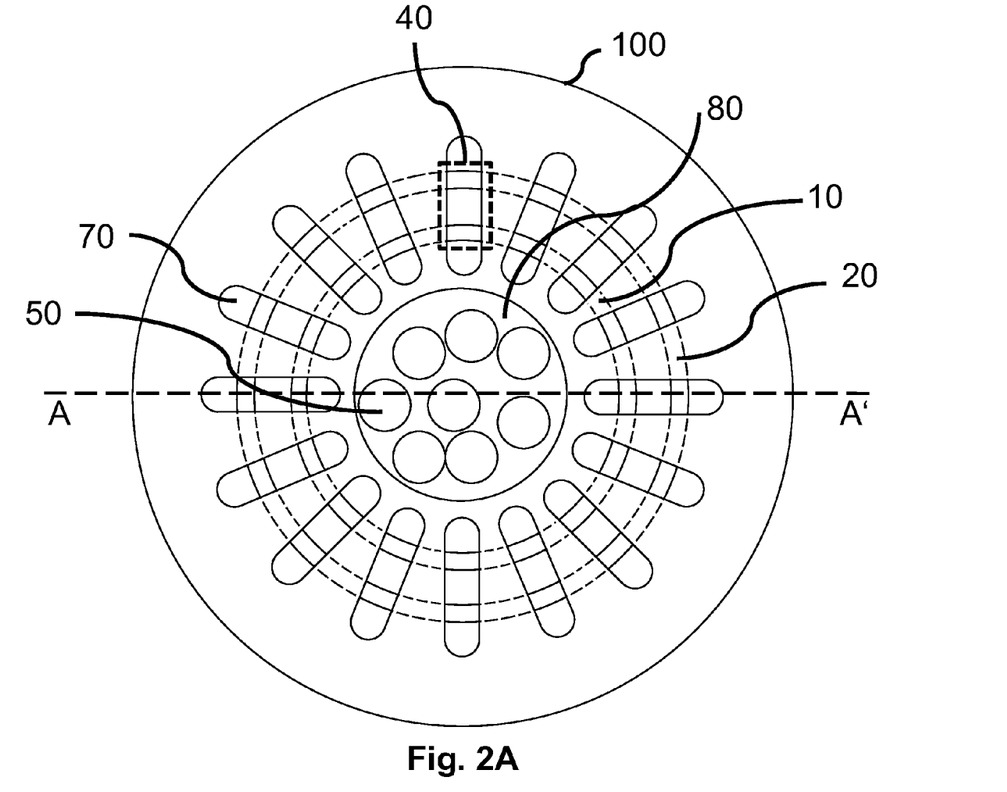
FIG. 2A shows a plan view of another embodiment of a sensor according to the present invention and FIG. 2B shows a cross section through a fluid channel of the sensor shown in FIG. 2A along line A-A'.
Figure 2B:
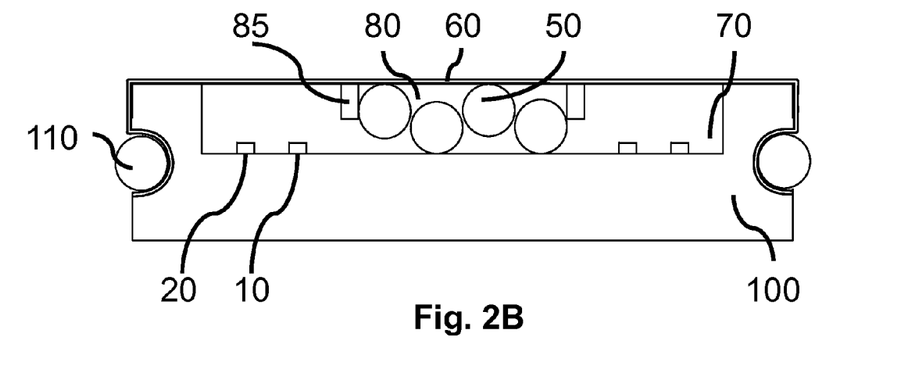

In FIGS. 2A and 2B, another embodiment of a sensor according to the present invention is shown. Here, the sensor comprises further a fluid reservoir 80, which is filled with ion-balancing means 50. As shown in FIG. 2A, the fluid reservoir 80 is arranged in the centre of the sensor with the electrodes 10 and 20 being arranged concentrically around. Furthermore, a plurality of fluid channels 70 are provided extending radially from the fluid reservoir 80 and crossing the electrodes 10 and 20 at detection sites 40 (indicated by a dashed box only once). The upper side of the fluid channels 70 is covered by the membrane 60, while the fluid channels 70 are separated from each other by channel walls of the housing 100. Thus, the large fluid volume in the fluid reservoir 80 is connected by the fluid channels 70 to the detection sites 40, so that sensor fluid 30 can be supplemented to the detection sites 40 from the fluid reservoir 80. Moreover, also the ion-balancing means 50 is in contact with the sensor fluid 30, so that polluting ions can be removed.

As shown in FIG. 2B illustrating a cross section along line A-A' of FIG. 2A, the ring-shaped electrodes 10 and 20 are arranged at the bottom of the sensor housing 100 for measuring the conductivity of the sensor fluid 30 at the detection sites 40. To obtain a response time of several minutes, the water layer thickness at the detection sites 40, i.e. the height of the fluid channels 70 defined by the distance between the membrane 60 and the bottom of the housing 100, should be at most of the order of one millimeter, as the $CO_2$ entering through the membrane 60 needs to diffuse through the sensor fluid 30 towards the electrodes 10 and 20.

In FIG. 2A, 2B, a bead-shaped ion-balancing means 50 is immobilized in the fluid reservoir 80, which is a semi-separated compartment filled with sensor fluid 30. That is, the sensor fluid 30 in the fluid reservoir 80 is connected to the sensor fluid 30 in the fluid channels 70 by openings or gaps near the bottom of the fluid reservoir 80. Of course, any other housing geometry is possible, e.g. a housing 100, wherein the fluid reservoir 80 is confined by walls having openings in the middle thereof. Likewise, the ion-balancing means 50 and the fluid reservoir 80 may be provided separately. The housing 100 may be made of plastic, for example PMMA. The openings can be smaller than the size of the ion-balancing means 50, so that the ion-balancing means 50 cannot escape from the fluid reservoir 80. However, the ion-balancing means 50 may also be immobilized using a mesh with holes smaller than the diameter of the ion-balancing means 50 or glue for preventing it to get into the fluid channels 70. Moreover, if the ion-balancing means 50 absorbs $HCO_3^-$, the distance between the ion-balancing means 50 and the electrodes 10 and 20 should be substantially larger than the fluid-layer thickness on the electrodes 10 and 20 at the detection sites 40 in order not to influence the measurement.

Here, the membrane 60 is attached to the sensor housing 100 with an O-ring 110 to avoid the use of potentially contaminating glue, but the membrane 60 could also be welded or glued. Between the fluid channels 70, the membrane 60 is supported by walls of the housing 100 defining the fluid channels 70 and also the fluid reservoir 80. Since the membrane 60 is very fragile due to its thickness of about 25 micrometers, the membrane 60 could come too close to the electrodes 10 and 20 or even break if such a reinforcement would be absent. Although it is shown in FIGS. 2A and 2B that the fluid reservoir 80 is covered by the membrane 60, this is not necessarily the case. Alternatively, the fluid reservoir 80 can be covered by a solid wall of the housing 100. In this case, the membrane 60 is further stabilized. Moreover, the ion-balancing means is not directly exposed to the gas exchange with the outside and fluid evaporation via the membrane 60 is reduced due to the reduced membrane-sensor fluid interface.

Parts of the fluid channels 70 may be made hydrophilic, e.g. the walls may be treated with a plasma, such as an oxygen or nitrogen plasma, or provided with a hydrophilic or hygroscopic coating. This ensures that, when sensor fluid 30 evaporates through the membrane 60 or escapes by other ways from the detection sites 40, the fluid channels 70 are automatically re-filled with sensor fluid 30. Thus, thanks to replenishment with sensor fluid 30 from the fluid reservoir 80, the electrodes 10 and 20 remain covered by sensor fluid 30 at least at the detection sites 40.

Figure 3A:
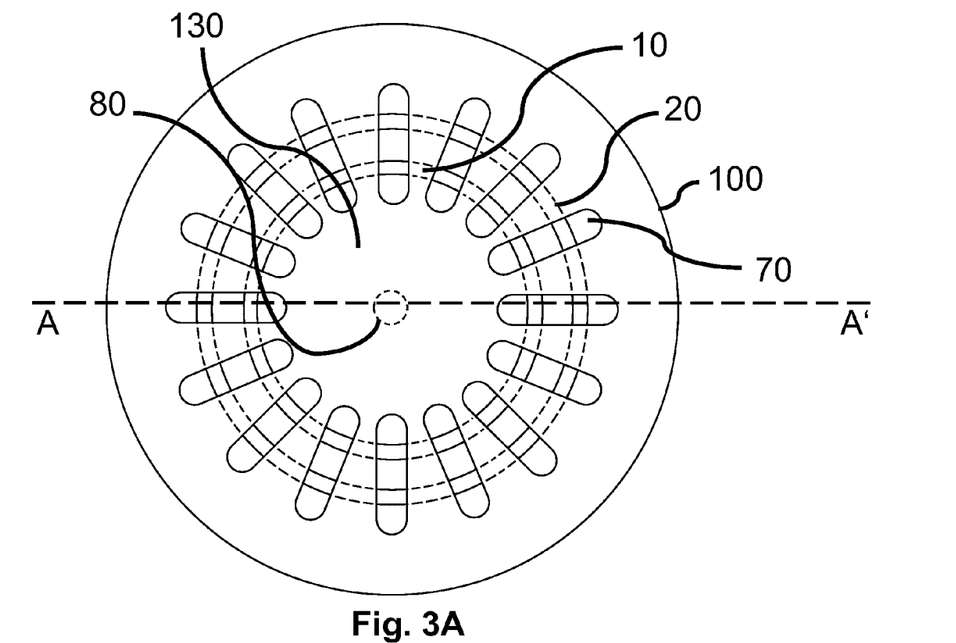
FIG. 3A shows a plan view of a sensor according to a further embodiment of the present invention and FIG. 3B shows a cross section through a fluid channel of the sensor shown in FIG. 3A along line A-A'.
Figure 3B:
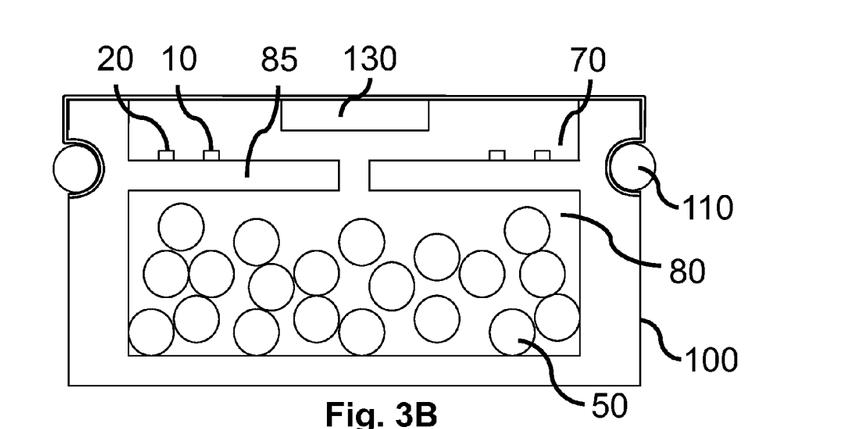

In FIG. 3, another embodiment of a sensor according to the present invention is shown. FIG. 3A shows a top view of the sensor with the membrane 60 being removed, while FIG. 3B shows a cross section through fluid channels 70 of the sensor along line A-A' shown in FIG. 3A. This embodiment differs from the one shown in FIG. 2A, 2B by a larger volume of the fluid reservoir 80 and by a longer distance between the fluid reservoir 80 comprising the ion-balancing means 50 and the electrodes 10 and 20. Here, the fluid reservoir 80 is arranged below the electrode arrangement and semi-separated from the fluid channels 70 by a reservoir wall 85 having an opening in the center. On top of the reservoir wall 85 or of the fluid reservoir 80, the concentrical electrodes 10 and 20 are arranged. The resulting longer distance between the ion-balancing means 50 and the electrodes 10 and 20 increases the time needed by ions to diffuse from one to the other. Since the electrodes 10 and 20 are much closer to the membrane 60 than to the ion-exchange resin 50, the measurement of the $CO_2$ pressure will hardly be influenced by the ion-balancing means 50. However, it will also take longer on average for polluting ions to be absorbed by the ion-balancing means 50. If there is only a slow leaching of ions, this is no problem. Moreover, the larger volume of the fluid reservoir 80 enables the storage of more material of ion-balancing means 50 and provides a larger volume of sensor fluid 30 for buffering fluid loss at the detection sites 40. In addition, as shown in FIG. 3B, the housing 100 may comprise an upper wall 130 covering the upper side of the sensor except for the top of the fluid channels 70, so that the fluid evaporation through the membrane can be further reduced.

Figure 4A:
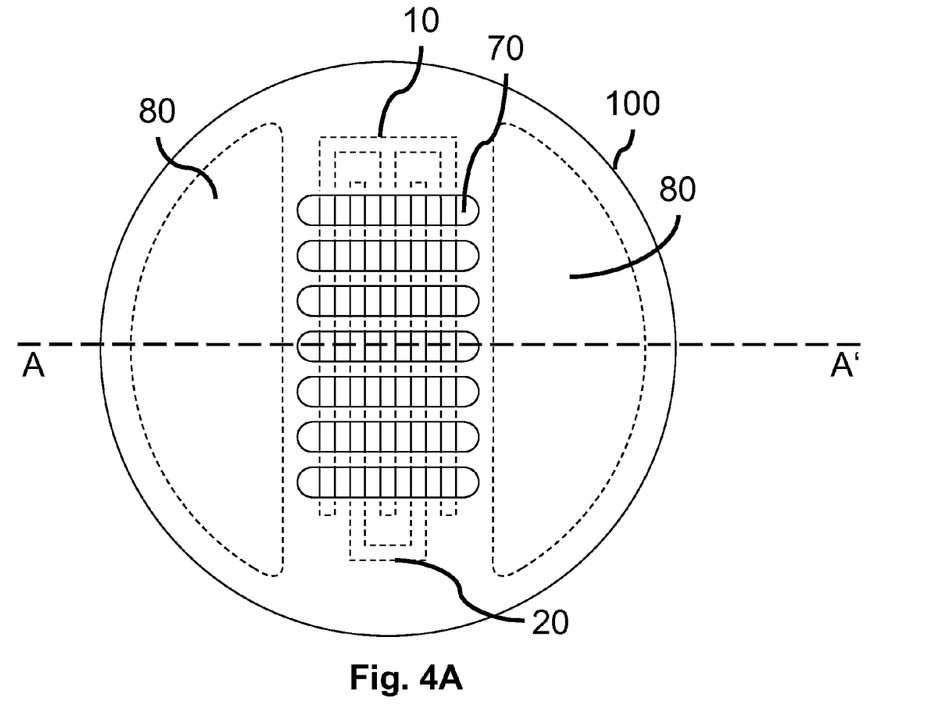
FIG. 4A shows a plan view of a sensor according to a further embodiment of the present invention and FIG. 4B shows a cross section through a fluid channel of the sensor shown in FIG. 4A along line A-A'.
Figure 4B:
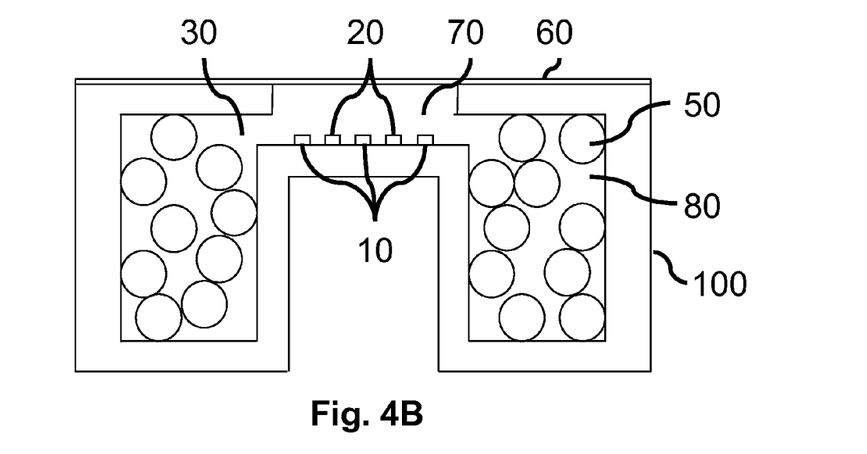

In FIG. 4, another embodiment of a sensor according to the present invention is shown, with the electrodes 10 and 20 arranged in a interdigitated or comb-like manner in the center of the housing 100. The fluid channels 70 are covered by the membrane 60 sealed on the top of the housing 100 and cross both electrodes 10 and 20, thus defining the detection sites 40 at the electrodes 10 and 20. Moreover, two separate fluid reservoirs 80 filled with sensor fluid 30 and ion-balancing means 50 are provided on either side of the electrodes 10 and 20. The fluid reservoirs 80 are configured as semi-separated compartments in the sensor housing 100 extending below the portion supporting the electrodes 10 and 20, i.e. below the sensing surface in the middle of the sensor. In other words, according to the embodiment shown in FIG. 4B, the housing 100 may be shaped like a box with a groove in the bottom surface, such that the cross section of the sensor housing 100 is shaped like an inverse rectangular U. The fluid reservoirs 80 are in the side parts of the U-shape, while the electrodes 10 and 20 as well as the fluid channels 70 are arranged in the middle part. The membrane 60 covers the top surface of the sensor and is in contact at least with the sensor fluid 30 in the fluid channels 70 via slits in the top surface of the housing 100. The openings, through which the fluid reservoirs 80 are connected to the fluid channels 70 and detection sites 40 (not shown in FIG. 4), are small enough that the ion-balancing means 50 cannot escape from the fluid reservoirs 80. As described before, at least one of the fluid channels 70 and area around the electrodes may be made hydrophilic, thus improving the fluid supply from the fluid reservoirs 80. The sensor design according to this embodiment allows furthermore easy initial cleaning by flushing sensor fluid 30 from one fluid reservoir 80 to the other via fluid ports (not shown) as well as bubble-free filling of the sensor with sensor fluid 30.

Figure 5A:
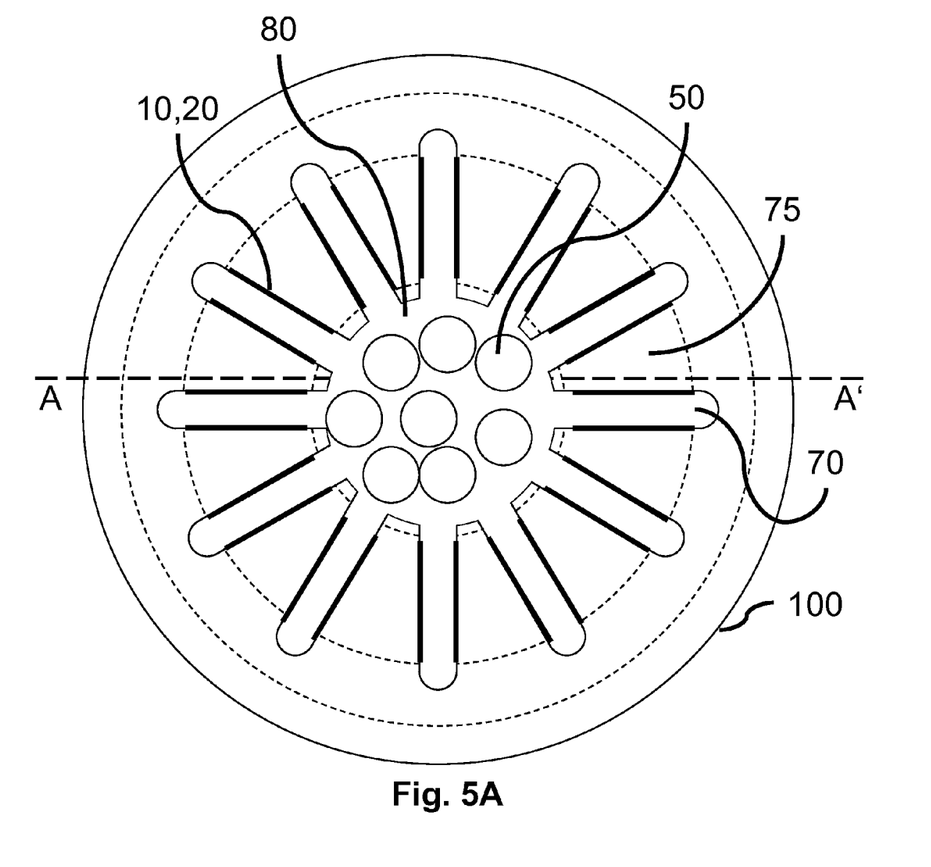
FIG. 5A shows a plan view of a sensor according to a further embodiment of the present invention and FIG. 5B shows a cross section between fluid channels of the sensor shown in FIG. 5A along line A-A'.
Figure 5B:
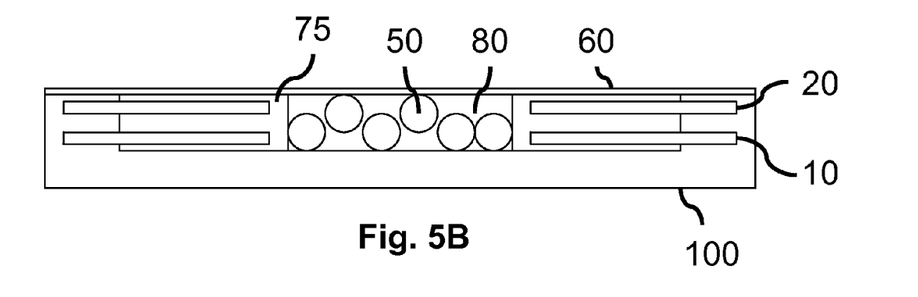

A further sensor design is shown in FIGS. 5A and 5B. Here, the fluid reservoir 80 including the ion-balancing means 50 is arranged in the center of the sensor housing 100. The upper side of the fluid reservoir 80 is covered by the membrane 60. From the fluid reservoir 80, the fluid channels 70 extend as star-like or radial slits in the top surface of the housing. In the plan view of FIG. 5A shown without membrane 60, the fluid channels 70 are open at the top and defined laterally by channel walls 75 of the housing 100. Within the material of the housing 100 forming the channel walls 75, the electrodes 10 and 20 are laminated, as can be better seen in the cross section shown in FIG. 5B. That is, the electrode 10 may be formed as a conductive layer on a layer of housing material and covered with another layer of isolating material (possibly the same as the housing material). Thereon, the second electrode 20 may be formed as a conductive layer and covered with another layer of housing material. Then, the assembly may be patterned in order to cut out the fluid channels 70 and the fluid reservoir. Of course, the electrodes 10 and 20 may also be otherwise attached at the surface of the channel walls 75. The channel walls 75 also define the planar dimensions of the fluid reservoir 80, i.e. they form the circumferential surface of the fluid reservoir 80. As shown in FIGS. 5A and 5B, the fluid channels 70 are too small to be entered by the ion-balancing means 50, so that the channel walls 75 immobilize the ion-balancing means 50 in the fluid reservoir 80. However, the ion-balancing means 50 may also be immobilized by other means, e.g. glue, a further membrane, or a mesh, as described above.

In all embodiments described here, the sensor may further comprise a release means (not shown in the figures) that allows the fluid reservoir 80 to actually release the sensor fluid 30 to the detection site 40. This may be invisible but may also be a noticeable feature in the sensor like a moveable or flexible wall of the fluid reservoir 80, a further compartement in contact with the fluid reservoir 80 or a pre-arranged site where a gas-bubble is trapped. The gas-bubble can easily grow as the sensor fluid 30 from the fluid reservoir 80 slowly replenishes any evaporation loss at the detection site 40. The gas-bubble can, for example, be left in a filling port, just before the sensor is closed off, or be inserted as part of a separate structure like a tiny piece of plastic tubing (e.g. between the ion-balancing means 50) that is hydrophobic and contains an air bubble. However, gas bubbles or a depressed membrane 60 at the detection site 40 should be avoided, so the release means may be arranged at a site in the fluid reservoir 80 that is more favorable for bubble-forming. For avoiding bubbles completely, a flexible fluid reservoir 80 may be used, filled with degassed sensor fluid 30 and packaged gas-tight. In case that the release means is realized as a compartment, it may be connected via one or more hydrophobic channel to the fluid reservoir 80. Moreover, the compartment of the release means may be flexible and/or hydrophobic, possibly comprising the gas-bubble described above. By these means, the volume change of sensor fluid 30 in the fluid reservoir 80 can be compensated when supplementing sensor fluid 30 to the measurement site 40.

Figure 6:
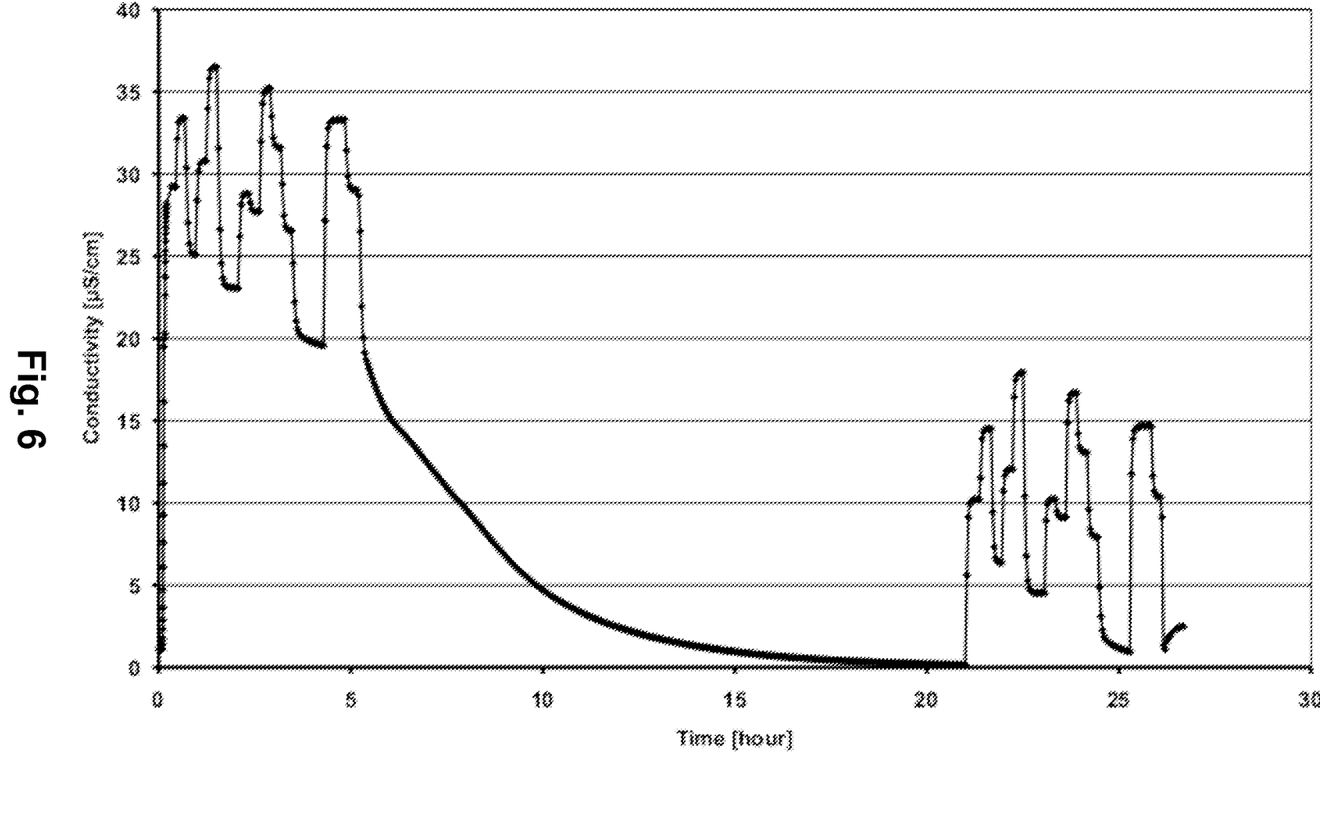
FIG. 6 shows a graph of conductivity as a function of time measured by a sensor according to the present invention.

In FIG. 6, the conductivity (in μS/cm) sensed by a sensor according to any embodiment of the present invention is plotted against time (in hours) while performing an experiment for checking, if the ion-balancing means 50 removes unwanted ions from the sensor fluid 30 and is still able to measure the amount of $CO_2$. At time 0 hours, an amount of ions, which may enter the sensor fluid 30 during storage of the sensor, is simulated by adding a grain of salt (NaCl) to clean water. After adding this grain of salt, the conductivity of the water used as sensor fluid 30 increased with 19 μS/cm. Subsequently, the $CO_2$ pressure is varied using a gas mixture of $CO_2$ and $N_2$ during 5 to 6 hours in steps of ca. 30 minutes and the fluctuating conductivity was measured. Then, ion-exchange resin was added as ion-balancing means 50 to the water and it was waited for 16 hours. During that period, the conductivity dropped almost to zero. Then again, the $CO_2$ pressure was varied during 5 to 6 hours in steps of ca. 30 minutes and the fluctuating conductivity was measured. This results in the conductivity measurement shown in FIG. 6. Hence, the ion-exchange resin 50 was able to remove the offset introduced by the polluting ions originating from the grain of salt.

Figure 7:
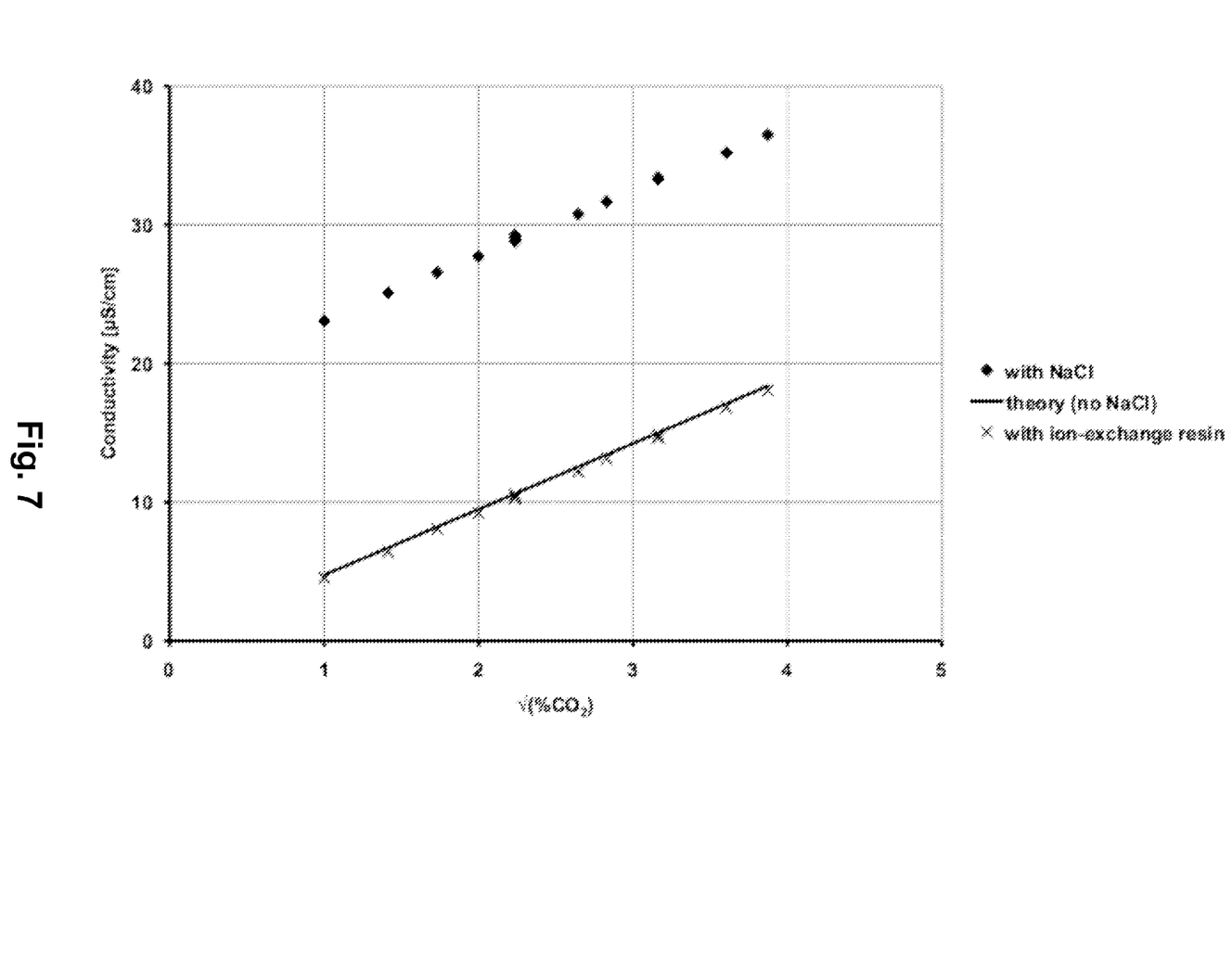
FIG. 7 shows a graph illustrating a relationship of water conductivity and the square root of percentage of $CO_2$ in a gas at atmospheric pressure and in equilibrium with the amount of dissolved $CO_2$ in water.

In FIG. 7, the relationship of water conductivity and the square root of the percentage of $CO_2$ in the gas, which is at atmospheric pressure and in equilibrium with the amount of dissolved $CO_2$ in the sensor fluid 30, is shown. The relationship between the conductivity of pure water and the partial $CO_2$ pressure, with which it is in equilibrium, is known and shown as a straight line in FIG. 7. The equilibrium values of the salted water are measured during the first 5 to 6 hours of the experiment described above and are shown as diamonds in FIG. 7 and the equilibrium values measured 15 hours after addition of ion-exchange resin 50 to the water 30 are shown in FIG. 7 as crosses. Within the uncertainty of the measurement, the crosses follow exactly the theoretical line. This shows that all the undesired or polluting ions have been absorbed by the ion-exchange resin 50 during the 16 hours after addition of the resin and that the conductivity measurement still responds to variations in $CO_2$ pressures, when $CO_2$ is fed to the system and varied in steps of half an hour. Therefore, in case of the initial fluid, i.e. the water with dissolved NaCl mimicking a sensor fluid 30 polluted by unwanted ions during storage, the sensor has to be callibrated before use to determine the relationship between conductivity and $CO_2$ pressure. In contrast, in case of using the final liquid as sensor fluid 30, i.e. the water with ion-exchange resin 50 having absorbed the $Na^+$ and $Cl^-$ ions, no such calibration is needed, because the theory is followed exactly. Therefore, by adding an ion-balancing means 50 such as ion-exchange resin to the sensor fluid 30, the sensor according to the present invention does not need calibration procedures before use. Moreover, it could be demonstrated that drift in such a sensor is negligible.

In a further embodiment, a system for ventilating and/or monitoring a patient is provided, wherein a sensor according to any of the above described embodiments is employed. The sensor according to the present invention can be applied to a conductometric transcutaneous $CO_2$ sensor integrable in a system. By these means, the $CO_2$ blood pressure of a patient, who is ventilated at home, can be measured continuously over night in order to see whether the ventilator settings are still correct.

It should be noted that features described for one embodiment mentioned above and shown in FIG. 1-5 can easily be exchanged with features of another embodiment. Thus, features of the above-described embodiments are arbitrarily combinable with each other. Moreover, the above-described embodiments of a sensor were mainly exemplified by conductometric $CO_2$ sensors. However, the principles of the invention can also be applied in other kinds of fluid-based sensors, namely potentiometric sensors. In that case, the type of ion-balancing means and/or the way it is separated from other parts of the sensor is more complicated, because the ions that are deliberately put in the electrolyte used as sensor fluid (for example $Cl^-$ for an AgCl reference electrode) should also remain uninfluenced by the ion-balancing means. This problem can be solved by using an ion-balancing means with low affinity for these ions and/or by separating this part of the sensor fluid from the ion-balancing means, which can be done with a solid wall or with a membrane that is impermeable for the ions that have to be kept intact. In addition, the invention can be applied in other sensors, i.e. sensors for measuring the concentration of ions like $Cl^-$, $F^-$, $Na^+$, and $NH_3^+$.

Hence, according to the present invention, drift of a fluid-based sensor can be drastically reduced due to counterbalancing ion pollution by adding ion-balancing means to a sensor fluid, so that calibration and re-membraning can be avoided. The ion-balancing means absorbs unwanted ions leaching out from the sensor housing or glue, while it leaves the ions originating from the gas to be measured intact on the appropriate time scales. For instance, changes in the gas concentration to be detected are designed to be on a shorter time scale than the time scale for the occurrence of contamination. Therefore, the addition of the ion-balancing means does not influence the measurement. The drift may be even further reduced by additionally compensating fluid loss using a fluid reservoir. Moreover, because the concept is cheap, the sensor device may be disposable. Hence, rather than carefully re-membraning the sensor, the entire assembly can be simply replaced.

Thus, in a most preferred embodiment, a non-invasive transcutaneous sensor for measuring blood gas concentration is provided, which is cheap and easy to use, conveyable to the patient by mail and attachable to the patient's skin by the patient himself, without intervention of a nurse or need for calibration and/or re-membraning.

The invention claimed is:

1. A sensor for measuring a concentration of fluid-soluble gas, comprising:
    a housing which is at least partially covered by a selective permeable membrane and filled with a sensor fluid;
    at least two electrodes arranged within the housing, said electrodes being covered by the sensor fluid at at one or more detection sites; and
    an ion-balancing means arranged within the housing and being spaced apart from the one or more detection sites of the electrodes and in contact with the sensor fluid for removing polluting ions from the sensor fluid.

2. The sensor according to claim 1, wherein a distance between the ion-balancing means and the detection site is larger than a thickness of the sensor fluid on the electrodes at the one or more detection sites such that the removal of polluting ions by the ion-balancing means occurs on a different timescale than measuring ions originating from the fluid-soluble gas.

3. The sensor according to claim 1, wherein an amount or kind of the ion-balancing means is adapted to at least one of type of the gas to be measured, type of the sensor fluid, type of the sensor and a geometry of the sensor.

4. The sensor according to claim 1, wherein the ion-balancing means includes at least one of an ion-trapping means, an ion-exchange polymer, an ion-exchange resin and a mixed-bed ion-exchange resin.

5. The sensor according to claim 1, wherein the electrodes are in a concentrical or interdigitated arrangement.

6. The sensor according to any claim 1, wherein the sensor comprises one or more fluid channels crossing the two electrodes at the at least one detection site, wherein the fluid channels extends radially from a fluid reservoir containing the ion-balancing means.

7. The sensor according to claim 1, wherein the sensor comprises further a substrate and the selective permeable membrane forming an external appearance thereof, wherein the membrane is permeable for neutral molecules in gas phase.

8. The sensor according to claim 1, wherein the sensor comprises further a fluid reservoir connected to the detection site for supplementing sensor fluid.

9. The sensor according to claim 8, wherein the fluid reservoir and the detection site are connected by at least one capillary, hydrophilic, or hygroscopic structure.

10. The sensor according to claim 8, wherein the ion-balancing means is arranged in the fluid reservoir.

11. The sensor according to claim 1, wherein the sensor is configured to perform measurements based on at least one of conductivity, potential difference, pH, optical properties of the sensor fluid and properties of a sensing substance in contact with the sensor fluid.

12. The sensor according to claim 1, wherein the sensor is a transcutaneous sensor for measuring blood gas concentrations that includes fixing means for fixing the sensor to a body tart of a patient.

13. The sensor according to claim 1, wherein the sensor is portable and includes a power source, a transmission unit to transmit sensed data to a remote reciever, and a chip operably coupled with the power source and the transmission unit, wherein the chip stores, transmits, and processes the sensed data.

14. The sensor according to claim 1, wherein a distance between the ion-balancing means and the detection site is larger than a distance between the electrodes such that the removal of polluting ions by the ion-balancing means is performed on a different timescale than measuring ions originating from the fluid-soluble gas.

15. A sensor for measuring a concentration of fluid-soluble gas associated with a patient, comprising:
    a housing at least partially covered by a selective permeable membrane, wherein the housing is filled with a sensor fluid;
    at least two concentric electrodes arranged within the housing, said concentric electrodes being in contact with the sensor fluid at one or more detection sites; and
    an ion-balancing means arranged within the housing and being spaced apart from the one or more detection sites of the concentric electrodes and in contact with the sensor fluid for removing polluting ions from the sensor fluid.

16. The sensor of claim 15, wherein the ion-balancing means is secured to the housing at a position within the at least two concentric electrodes.

17. A sensor for measuring a concentration of fluid-soluble gas associated with a patient, comprising:

a housing at least partially covered by a selective permeable membrane, wherein the housing is filled with a sensor fluid;

an interdigitated arrangement of at least two electrodes within the housing, said interdigitated arrangement of electrodes being covered by the sensor fluid at one or more detection sites; and an ion-balancing means arranged within the housing and being spaced apart from the one or more detection sites of the interdigitated arrangement electrodes and in contact with the sensor fluid for removing polluting ions from the sensor fluid.

18. The sensor of claim 16, wherein the ion-balancing means is secured to the housing at positions on either side of the interdigitated arrangement of electrodes.

* * * * *